(12) United States Patent
Tracy et al.

(10) Patent No.: US 11,466,294 B2
(45) Date of Patent: *Oct. 11, 2022

(54) SUPPLEMENTED MIXOTROPHIC FERMENTATION METHOD

(71) Applicant: SUPERBREWED FOOD INC., New Castle, DE (US)

(72) Inventors: Bryan Patrick Tracy, Wilmington, DE (US); Shawn William Jones, Bear, DE (US); Aharon M. Eyal, Jerusalem (IL)

(73) Assignee: SUPERBREWED FOOD INC., New Castle, DE (US)

( * ) Notice: Subject to any disclaimer, the term of this patent is extended or adjusted under 35 U.S.C. 154(b) by 271 days.

This patent is subject to a terminal disclaimer.

(21) Appl. No.: 16/306,186

(22) PCT Filed: May 31, 2017

(86) PCT No.: PCT/US2017/035219
§ 371 (c)(1),
(2) Date: Nov. 30, 2018

(87) PCT Pub. No.: WO2017/210296
PCT Pub. Date: Dec. 7, 2017

(65) Prior Publication Data
US 2021/0024962 A1 Jan. 28, 2021

Related U.S. Application Data

(60) Provisional application No. 62/344,163, filed on Jun. 1, 2016, provisional application No. 62/345,439, filed on Jun. 3, 2016, provisional application No. 62/349,362, filed on Jun. 13, 2016, provisional application No. 62/411,043, filed on Oct. 21, 2016.

(51) Int. Cl.
*C12P 7/06* (2006.01)
*C12P 7/14* (2006.01)

(52) U.S. Cl.
CPC ............... *C12P 7/065* (2013.01); *C12P 7/14* (2013.01)

(58) Field of Classification Search
CPC ................................. C12P 7/065; C12P 7/14
See application file for complete search history.

(56) References Cited

U.S. PATENT DOCUMENTS

| | | | |
|---|---|---|---|
| 4,578,353 A | 3/1986 | Assarsson et al. | |
| 7,285,402 B2* | 10/2007 | Gaddy | C12M 29/02 435/162 |
| 8,759,070 B2* | 6/2014 | Papoutsakis | C12P 7/52 435/252.2 |
| 9,938,542 B2* | 4/2018 | Tracy | C12P 7/54 |
| 2009/0093027 A1 | 4/2009 | Balan et al. | |
| 2010/0071262 A1 | 3/2010 | Robinson et al. | |
| 2011/0059499 A1 | 3/2011 | Simpson et al. | |
| 2011/0256600 A1 | 10/2011 | Simpson et al. | |
| 2012/0159839 A1 | 6/2012 | Koskinen et al. | |

FOREIGN PATENT DOCUMENTS

WO 2017/205363 11/2017

OTHER PUBLICATIONS

Blair et al., Carbon isotopic fractionation in heterotrophic nicrobial metabolism. Appl. Environ. Microbiol., 1985, vol. 50(4): 996-1001. (Year: 1985).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Fast et al., Stoichiometric and energetic analyses of non-photosynthetic CO2-fixation pathways to support synthetic biology strategies for production of fuels and chemicals. Curr. Opin. Chem. Eng., 2012, vol. 1: 380-395. (Year: 2012).*
Gehring T., Ph.D. Thesis, Gesellschaft zur Förderung des Lehrstuhls für Siedlungswasserwirtschaft und Umwelttechnik an der Ruhr-Universität Bochum e.V. Bochum, Germany, 2015, pp. 1-180. (Year: 2015).*
Kisselev L., Polypeptide release factors in prokaryotes and eukaryotes: same function, different structure. Structure, 2002, vol. 10: 8-9. (Year: 2002).*
Nagarajan et al., Characterizing acetogenic metabolism using a genome-scale metabolic reconstruction of Clostridium Ijungdahlii. Microbial Cell Factories, 2013, vol. 12:118, pp. 1-13. (Year: 2013).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Whitham J.M., Ph.D. Thesis, North Carolina State Univ., 2015, pp. 1-236. (Year: 2015).*

(Continued)

*Primary Examiner* — Ganapathirama Raghu
(74) *Attorney, Agent, or Firm* — Eva Taksel

(57) ABSTRACT

Supplemented mixotrophic method. A mixotrophic fermentation method is disclosed including providing a naturally acetogenic organism; providing a fermentation medium comprising a carbon source and a supplemented non-sugar reductant; and culturing the organism in the fermentation medium, where both the carbon source and the non-sugar reductant are metabolized and a fermentation broth is formed, which contains at least one carbon-containing bioproduct.

7 Claims, No Drawings

(56) References Cited

OTHER PUBLICATIONS

Wishart et al., A single mutation converts a novel phosphotyrosine binding domain into a dual-specificity phosphatase. J. Biol. Chem., 1995, vol. 270(45): 26782-26785 (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
O'Leary, "Carbon Isotopes in Photosynthesis: Fractional Techniques May Reveal New Aspects of Carbon Dynamics in Plants", *BioScience* 38(5):328-336, 1988.
Liew et al., "Gas Fementation—A Flexible Platform for Commercial Scale Production of Low-Carbon-Fuels and Chemicals from Waste and Renewable Feedstocks", *Front Microbiol.* 7:694, 2016.
International Search Report and Written Opinion of the ISA issued in PCT/US2017/035219, dated Sep. 6, 2017.
U.S. Appl. No. 62/411,043, filed Oct. 21, 2016.
U.S. Appl. No. 62/349,362, filed Jun. 13, 2016.
U.S. Appl. No. 62/345,439, filed Jun. 3, 2016.
U.S. Appl. No. 62/344,163, filed Jun. 1, 2016.

\* cited by examiner

SUPPLEMENTED MIXOTROPHIC FERMENTATION METHOD

CROSS REFERENCE TO RELATED APPLICATIONS

The instant application claims priority to U.S. Provisional Application No. 62/344,163, filed Jun. 1, 2016; U.S. Provisional Application No. 62/345,439, filed Jun. 3, 2016; U.S. Provisional Application No. 62/349,362, filed Jun. 13, 2016; and U.S. Provisional Application No. 62/411,043, filed Oct. 21, 2016, the disclosures of each of which are incorporated by reference herein in their entireties.

FIELD OF THE INVENTION

The field of art to which this invention generally pertains is the production of bioproducts using microorganisms.

BACKGROUND

To reduce microbial fermentation production costs for certain bioproducts used in biofuels and other applications, attempts have been made to maximize feedstock conversion to the product or products of interest. However, these attempts have been fraught with difficulties. For example, attempts to ferment gaseous substrates with autotrophic organisms have been hindered by difficulties in reaching suitable concentrations of the substrate and by low titers, which increase isolation-related operating costs. Autotrophic fermentation has also been limited in the range of economically attainable products.

Mixotrophic fermentation involves the concurrent use of organic substrates (e.g., sugars) and inorganic substrates (e.g., $CO_2$, CO, $H_2$) for growth and metabolism. Mixotrophic fermentation, which therefore combines aspects of autotrophic fermentation and heterotrophic fermentation, has also been utilized for the production of bioproducts and has advantages over, for example, autotrophic fermentation. For example, mixotrophic fermentation may result in reduced loss of $CO_2$ produced during fermentation, thereby allowing more complete conversion of an initial carbon source into acetyl-CoA and/or other bioproducts.

However, there remains a need for fermentation methods—including mixotrophic fermentation methods—and engineered metabolic pathways that minimize $CO_2$ losses and that result in even greater feedstock conversion. Ideally, such methods would eliminate $CO_2$ losses altogether and result, for example, in complete conversion of a carbohydrate source into acetyl-CoA and/or other desired bioproducts. There also remains a need for reducing feedstock and feedstock pre-treatment costs for use in microbial fermentation methods of bioproducts, which costs can affect the economic viability of cellulosic and other next generation biofuel manufacturing processes.

SUMMARY OF THE INVENTION

A supplemented mixotrophic fermentation method is disclosed including providing a naturally acetogenic organism; providing a fermentation medium comprising a carbon source that is metabolized by the native form of the organism at a maximum rate of less than 0.01 g/hr/g cell mass and a non-sugar reductant; and culturing the organism in a fermenter with the fermentation medium, whereby both the carbon source and the non-sugar reductant are metabolized and a fermentation broth is formed, which broth comprises at least one carbon-containing bioproduct.

Additional embodiments include: the method disclosed above where the bioproduct comprises ethanol and wherein the carbon yield, based on the total amount of carbon in produced ethanol divided by the total amount of carbon metabolized from said carbon source, is at least 67%; the method disclosed above where the carbon source comprises a sugar and total reductant efficiency is at least 67%; the method disclosed above where the carbon source comprises a sugar and/or glycerol; the method disclosed above where said fermentation medium further comprises $CO_2$; the method disclosed above comprising exogenously supplementing at least a portion of the $CO_2$; the method disclosed above where said reductant comprises CO, methanol and/or $H_2$; the method disclosed above where said reductant comprises $H_2$; the method disclosed above where said carbon source comprises a sugar, said reductant comprises $H_2$, and the weight/weight ratio between said sugar and said $H_2$ is in the range between 1.2 and 150; the method disclosed above where said organism is a genetically modified organism; the method disclosed above where said bioproduct is selected from the group consisting of ethanol, lactic acid, acetic acid, 2,3-butanediol, and mixtures thereof; the method disclosed above where said bioproduct comprises ethanol; the method disclosed above where the carbon yield, based on the total amount of carbon in produced bioproducts divided by the total amount of carbon metabolized from said carbon source, is at least 50%; the method disclosed above where the carbon source comprises a sugar and where total reductant efficiency is greater than 100% of the reductant efficiency the sugar alone could provide; the method disclosed above where $CO_2$ is emitted from the fermenter during culturing and the weight/weight ratio between the amount of bioproduct in said fermentation broth and the amount of emitted $CO_2$ is greater than 1.05; the method disclosed above where said fermentation broth further comprises acetic acid as a second bioproduct and where the amount of acetic acid produced per biomass unit weight is less than about 50% of that produced in autotrophic fermentation with the same organism under the same conditions; the method disclosed above where said fermentation medium comprises stillage of ethanol production; the method disclosed above further comprising gasification of a corn processing co-product, whereby said non-sugar reductant is generated; and the method disclosed above co-located with ethanol production.

A supplemented mixotrophic fermentation method is disclosed including providing a naturally acetogenic organism capable of producing ethanol; providing a fermentation medium comprising a carbon source and a non-sugar reductant wherein said carbon source comprises a sugar that is metabolized by the native form of the organism at a maximum rate of less than 0.01 g/hr/g cell mass; and wherein said non-sugar reductant comprises $H_2$ at weight/weight ratio between said sugar and said $H_2$ in the range between 1.20 and 150; and culturing said organism in said fermentation medium, whereby both the carbon source and the non-sugar reductant are metabolized and a fermentation broth comprising ethanol is formed, and where: a. the carbon yield based on the total amount of carbon in produced ethanol divided by the total amount of carbon metabolized from said carbon source is at least 67%; b. the total reductant efficiency is at least 67%; and/or c. $CO_2$ is emitted from a fermenter during culturing and a weight/weight ratio between ethanol in said fermentation broth and the amount of emitted $CO_2$ is greater than 1.05.

Additional embodiments include: the method disclosed above including at least two of said a, b and c; the method disclosed above including all three of said a, b and c; the method disclosed above where said organism is a genetically modified organism; the method disclosed above where said fermentation medium comprises a steel mill produced composition containing CO; the method disclosed above where said non-sugar reductant additionally includes CO, methanol, or a combination thereof, and wherein the $^{13}C/^{12}C$ isotope ratio of the carbon present in said non-sugar reductant is less than that of atmospheric $CO_2$; the method above including adding to said fermentation medium a mixture of $CO_2$ and hydrogen at a molar ratio in the range of from 1:0.1 to 1:15; the method disclosed above where the sugar comprises glucose and/or sucrose, where metabolizing the sugar produces $CO_2$, and where the organism metabolizes the $CO_2$ produced; the method disclosed above where the sugar comprises glucose and/or sucrose, the non-sugar reductant further comprises CO and/or methanol, metabolizing the sugar produces $CO_2$, and the organism metabolizes the $CO_2$ produced; the method disclosed above where said fermentation medium comprises stillage of ethanol production; the method disclosed above further comprising gasification of a corn processing co-product, whereby said non-sugar reductant is generated; and the method disclosed above co-located with ethanol production.

An integrated method for producing ethanol is also disclosed, the method comprising (i) fermenting liquefied corn with a first organism, which first organism is ethanol producing, to form a first ethanol-comprising fermentation broth; (ii) distilling ethanol from said first ethanol-comprising fermentation broth to form distilled ethanol and a carbon-source comprising whole stillage; (iii) providing a second organism, which second organism is naturally acetogenic and ethanol producing; (iv) providing a fermentation medium comprising said carbon source and a non-sugar reductant wherein said carbon source further comprises a sugar that is metabolized by the native form of the second, naturally acetogenic organism at a maximum rate of less than 0.01 g/hr/g cell mass; and wherein said non-sugar reductant comprises $H_2$ at a weight/weight ratio between said sugar and said $H_2$ in the range between 1.20 and 150; and (v) culturing said second, naturally acetogenic organism in said fermentation medium, whereby both the carbon source and the non-sugar reductant are metabolized and a second fermentation broth comprising ethanol is formed, and wherein: (a) the carbon yield based on the total amount of carbon in produced ethanol divided by the total amount of carbon metabolized from said carbon source is at least 67%; (b) the total reductant efficiency is at least 67%; and/or (c) $CO_2$ is produced during fermentation by the organism from either the carbon source or the non-sugar reductant, and a weight/weight ratio between ethanol in said fermentation broth and produced $CO_2$ is greater than 1.05.

Additional embodiments include: the method disclosed above including at least two of said a, b and c; the method disclosed above including all three of said a, b and c; the method disclosed above where said second, naturally acetogenic organism is a genetically modified organism; the method disclosed above where said fermentation medium comprises a steel mill produced composition containing CO; the method disclosed above where said non-sugar reductant additionally includes CO and/or methanol, and where the $^{13}C/^{12}C$ isotope ratio of the carbon present in said non-sugar reductant is less than that of atmospheric $CO_2$; the method disclosed above comprising providing said fermentation medium with a mixture of $CO_2$ and hydrogen at a molar ratio in the range from 1:0.1 to 1:15; the method disclosed above where the carbon source comprises glucose and/or sucrose, metabolizing the sugar produces $CO_2$, and the second, naturally acetogenic organism metabolizes the $CO_2$ produced; the method disclosed above further comprising gasification of a corn processing co-product, whereby said non-sugar reductant is generated; and the method described above where the fermentation medium comprises a sugar in addition to the sugar present in said carbon source comprising whole stillage and/or said carbon source comprising thin stillage; the method described above further comprising separating solids from said whole stillage to form distillers solids and a carbon source comprising thin stillage; the method described above where the fermentation medium comprises the non-sugar reductant, the carbon source comprising whole stillage, and the carbon source comprising thin stillage and both carbon sources are metabolized.

These and additional embodiments are disclosed herein in greater detail below.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be disclosed by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

Provided is an integrated supplemented mixotrophic fermentation method comprising providing a naturally acetogenic organism; providing a fermentation medium comprising a carbon source that is metabolized by the native form of the organism at a maximum rate of less than 0.01 g/hr/g cell mass and a supplemented non-sugar reductant comprising hydrogen, CO, methanol and or/mixtures thereof; wherein said providing a hydrogen; and culturing the organism in the fermentation medium, whereby both the carbon source and the non-sugar reductant are metabolized and a fermentation broth is formed, which broth comprises at least one carbon-containing bioproduct. As used herein, the term reductant refers to a reducing chemical or a chemical capable of providing electrons in a chemical reaction, for example with an oxidizing chemical that accepts the electrons. In a reaction between hydrogen and oxygen to form water, hydrogen is the reductant or reducing chemical and oxygen is the oxidizing chemical.

According to an aspect, provided is supplemented mixotrophic fermentation method comprising providing a naturally acetogenic organism capable of producing ethanol; providing a carbon source and a non-sugar reductant wherein said carbon source comprises a sugar that is metabolized by the native form of the organism at a maximum rate of less than 0.01 g/hr/g cell mass; and wherein said non-sugar reductant comprises $H_2$ at weight/weight ratio between said provided sugar and said provided $H_2$ in the range between 1.20 and 150; and culturing said organism in said fermentation medium, whereby both the carbon source and the non-sugar reductant are metabolized and a fermentation broth comprising ethanol is formed, and wherein: (a) the carbon yield based on the total amount of carbon in produced ethanol divided by the total amount of carbon metabolized from said carbon source is at least 67% (e.g., >69%, >71%, >73%, >75%); (b) the total reductant efficiency is at least 67% (e.g.: >70%, >75%>78%, >81%, >84%, >87%, >90%, >91%, >92%, >93%, >94%, >95%); and/or (c) $CO_2$ is produced during fermentation by the organism from the either the carbon source or the non-sugar reductant metabolized, and a weight/weight ratio between ethanol in said fermentation broth and produced CO2 is greater than 1.05. According to an embodiment, said method includes at least two of said (a), (b) and (c) or all three.

According to an aspect, provided is an integrated method for producing ethanol, comprising (i) fermenting liquefied corn with an ethanol producing organism to form a first ethanol-comprising fermentation broth; (ii) distilling ethanol from said first ethanol-comprising fermentation broth to form distilled ethanol and a carbon-source comprising whole stillage; (iii) optionally separating solids from said whole stillage to form distillers solids and a carbon-source comprising thin stillage; (iv) providing a naturally acetogenic organism capable of producing ethanol; (v) providing a fermentation medium comprising said carbon-source comprising whole stillage and/or said carbon-source comprising thin stillage and optionally an additional sugar and a non-sugar reductant wherein said carbon source comprises a sugar that is metabolized by the native form of the naturally acetogenic organism at a maximum rate of less than 0.01 g/hr/g cell mass; and wherein said non-sugar reductant comprises $H_2$ at weight/weight ratio between said provided carbon source and said provided $H_2$ in the range between 1.20 and 150; and (vi) culturing said organism in said fermentation medium, whereby both the carbon source and the non-sugar reductant are metabolized and a second fermentation broth comprising ethanol is formed, and wherein: (a) the carbon yield based on the total amount of carbon in produced ethanol divided by the total amount of carbon metabolized from said carbon source is at least 67% (e.g., >69%, >71%, >73%, >75%); (b) the total reductant efficiency is at least 67% (e.g., >70%, >75%>78%, >81%, >84%, >87%, >90%, >91%, >92%, >93%, >94%, >95%); and/or (c) $CO_2$ is produced during fermentation by the organism from either the carbon source or the non-sugar reductant, and a weight/weight ratio between ethanol in said fermentation broth and produced $CO_2$ is greater than 1.05. According to an embodiment, said method includes at least two of said (a), (b) and (c) or all three.

Organism Exemplary Embodiments

The method comprises providing a, naturally acetogenic organism. An organism is "naturally acetogenic" if the wild-type (or native) organism is capable of metabolizing $CO_2$ into acetate using the Wood-Ljungdahl pathway (or reductive acetyl-CoA pathway). A naturally acetogenic organism may be a wild-type organism or genetically modified. The CO, is emitted during culturing and the weight/weight ratio between the amount of bioproduct in said fermentation broth and the amount of emitted $CO_2$ is greater than 1.05, greater than 1.1, 1.2, greater than 1.3, greater than 1.4, greater than 1.5, greater than 2, greater than 2.2, greater than 2.4, greater than 2.6, greater than 2.8, greater than 3.0, greater than 3.5, greater than 4.0, greater than 4.5, or greater than 5.

According to an embodiment, said organism is of the Clostridia class. According to an embodiment, said organism is acetogenic Clostridia. According to an embodiment, said organism is a genetically modified Clostridia.

According to an embodiment, the organism may be selected from the group consisting of *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii, Sporomusa ovata, Thermacetogenium phaeum, Acetobacterium carbinolicum, Oxobacter pfennigii, Sporomusa termitida, Moorella glycerini, Eubacterium aggregans, Treponema azotonutricium, Terrisporobacter glycolicus,* and *Thermoanaerobacter kivui.*

The organism may be genetically modified. For example, the organism may be genetically modified to reduce or eliminate expression of a primary alcohol dehydrogenase or a secondary alcohol dehydrogenase. In an embodiment, the organism may be genetically modified to have a primary alcohol dehydrogenase gene or a secondary alcohol dehydrogenase gene deleted from its genome. While a genomic deletion is a preferred embodiment, any genomic mutation resulting in inactivation of the enzyme would be sufficient, including but not limited to partial gene deletion, nonsense mutation, transcriptional promoter deletion, etc. In another embodiment, the transcriptional expression of this gene can be reduced by using antisense RNA.

Providing a Fermentation Medium Exemplary Embodiments

According to an embodiment, said providing a fermentation medium comprising a non-sugar reductant further comprises at least one of (a) hydrocarbon reforming, (b) biomass-derived liquid reforming; (c) partial oxidation; (d) biomass gasification, (e) coal gasification, and (f) water-gas shift reaction.

According to an embodiment, said providing a fermentation medium comprising a non-sugar reductant comprises water-gas shift reaction. As used herein, the term water-gas shift reaction refers to the reaction between CO and water, wherein $CO_2$ and hydrogen are formed. According to an embodiment, water is introduced to the reaction as steam. According to an embodiment, a catalyst is used.

$$CO+H_2O \rightarrow CO_2+H_2$$

According to an embodiment, carbon dioxide and other impurities are removed from the gas stream, e.g. via pressure-swing adsorption, leaving essentially pure hydrogen.

According to an embodiment, said providing a fermentation medium comprising a non-sugar reductant comprises hydrocarbon reforming, wherein a hydrocarbon reacts with water. According to an embodiment, said hydrocarbon comprises methane. Any source of methane is suitable. According to an embodiment, methane is provided as natural gas. According to another embodiment, the method further comprises anaerobic fermentation, wherein methane is formed. According to an embodiment, high-temperature steam (e.g. at 700° C.) reacts with methane under pressure, optionally in the presence of a catalyst, whereby hydrogen and carbon monoxide are formed. According to an embodiment, the method further comprises reacting at least a fraction of said formed carbon monoxide with steam according to the water-gas shift reaction.

$$CH_4+H_2O \rightarrow CO+3H_2$$

$$CO+H_2O \rightarrow CO_2+H_2$$

According to an embodiment, said providing a fermentation medium comprising a non-sugar reductant comprises biomass-derived liquid reforming. According to an embodiment, said method comprises converting biomass into a product (e.g. ethanol, bio-oils) and reforming said product to produce hydrogen and CO. According to an embodiment, the method further comprises reacting at least a fraction of said formed carbon monoxide with steam according to the water-gas shift reaction.

$$C_2H_5OH+H_2O \rightarrow 2CO+4H_2$$

$$CO+H_2O \rightarrow CO_2+H_2$$

According to an embodiment, said providing a fermentation medium comprising a non-sugar reductant comprises partial oxidation. According to an embodiment, a hydrocarbon, e.g. methane reacts with a limited amount of oxygen to generate hydrogen and carbon monoxide. According to an embodiment, the method further comprises reacting at least a fraction of said formed carbon monoxide with steam according to the water-gas shift reaction.

$$CH_4+\tfrac{1}{2}O_2 \rightarrow CO+2H_2$$

$$CO+H_2O \rightarrow CO_2+H_2$$

In this way, for example, oxygen can be used to generate more $H_2$.

According to an embodiment, said providing a fermentation medium comprising a non-sugar reductant comprises gasification or partial oxidation of biomass. According to an embodiment, said biomass comprises cellulose. According to an embodiment, said biomass comprises lignin. According to an embodiment, said biomass comprises corn processing co-product, e.g. corn fibers, corn stover, corn cobs or mixtures thereof. According to an embodiment, biomass is reacted with a controlled amount of oxygen and/or steam into carbon monoxide, hydrogen, and carbon dioxide. According to an embodiment, the method further comprises reacting at least a fraction of said formed carbon monoxide with steam according to the water-gas shift reaction.

$$(C_6H_{10}O_5)n+O_2+H_2O \rightarrow CO+CO_2+H_2 \text{ (shown for cellulose, not balanced)}$$

$$CO+H_2O \rightarrow CO_2+H_2$$

According to an embodiment, said providing a fermentation medium comprising a non-sugar reductant comprises coal gasification. According to an embodiment, hydrogen is produced by first reacting coal with oxygen and steam under high pressures and temperatures to form synthesis gas. According to an embodiment, the method further comprises reacting at least a fraction of said formed carbon monoxide with steam according to the water-gas shift reaction.

$$CH_{0.8}+O_2+H_2O \rightarrow CO+CO_2+H_2 \text{ (not balanced)}$$

$$CO+H_2O \rightarrow CO_2+H_2$$

According to an embodiment, said providing a fermentation medium comprising a non-sugar reductant comprises at least one of partial oxidation and biomass gasification. According to an embodiment, said providing a non-sugar reductant comprises reaction with oxygen. According to an embodiment, said providing a non-sugar reductant comprises electrolysis, which electrolysis generates oxygen and at least a fraction of said generated oxygen is used for further providing said non-sugar reductant. According to an embodiment, said providing a non-sugar reductant comprises electrolysis and at least one of partial oxidation and biomass gasification, electrolysis generates oxygen and at least a fraction of said generated oxygen is used for at least one of partial oxidation and biomass gasification.

According to an embodiment, said method further comprises processing a lignocellulosic biomass to produce a separated carbohydrate solution and separated lignin and using said separated carbohydrate solution in said providing a carbon source. As used herein, the term lignocellulosic biomass refers to biomass comprising cellulose and lignin. According to an embodiment, the processed lignocellulosic biomass further comprises hemicellulose. According to an embodiment, said processing a lignocellulosic biomass comprises hydrolysis of hemicellulose, hydrolysis of cellulose or both. According to an embodiment, said hydrolysis comprises at least one of hydro-thermal treatment, acid-catalyzed hydrolysis and enzyme-catalyzed hydrolysis. According to an embodiment, said processing further comprises separating said carbohydrate solution from said lignin to form separated carbohydrate solution and separated lignin.

According to an embodiment said separated carbohydrate solution is used, as such or after modification, to form said fermentation medium carbon source. According to an embodiment, said method further comprises treating said separated carbohydrate solution for removal of solutes that hinder fermentation, e.g. furfural. According to an embodiment, said fermentation medium further comprises a nitrogen source.

According to an embodiment, said method comprises processing a lignocellulosic biomass to produce a separated carbohydrate solution and separated lignin and further comprises gasifying at least a fraction of said separated lignin for providing said non-sugar reductant.

According to an embodiment, said fermentation medium comprises a carbon source selected from carbohydrates, glycerol, methanol and combinations thereof. According to an embodiment, said carbon source is selected from glucose and sucrose.

According to an embodiment, said carbohydrate comprises monosaccharides, such as glucose, fructose and xylose, disaccharides, such as sucrose, oligosaccharides, such as dextrins, polysaccharides, such as starch, xylan, cellulose and hemicellulose and combinations thereof. According to an embodiment, said carbohydrate comprises hexoses, such as glucose and fructose, pentoses, such as xylose and arabinose and combinations thereof.

According to an embodiment, said organism metabolizes $CO_2$ produced on metabolizing said carbon source.

According to an embodiment, said provided carbon source, said provided non-sugar reductant or both comprise supplemented $CO_2$. As used herein, the term supplemented $CO_2$ refers to $CO_2$ other than that generated on metabolizing said carbon source carbon source. According to an embodiment, said supplemented $CO_2$ is generated in another fermentation process, e.g. in a conventional heterotrophic fermentation for ethanol production.

According to an embodiment, said fermentation medium further comprises CO. According to an embodiment, said fermentation medium further comprises a steel mill-produced CO composition. According to an embodiment, the fermentation medium may further comprise a steel mill gas composition. For example, the fermentation medium may comprise a steel mill gas composition comprising 40-80% CO, 10-25% $CO_2$, 2-5% $H_2$, and 15-35% $N_2$. In an embodiment, the fermentation medium may comprise a steel mill gas composition comprising 60-70% CO, 15-20% $CO_2$, 3-4% $H_2$, and 20-30% $N_2$. In an embodiment, the fermentation medium may comprise a steel mill gas composition comprising 43-55% CO, 17-20% $CO_2$, 2-3% $H_2$, and 25-34% $N_2$.

According to an embodiment, said organism is acetogenic and said carbon source comprises at least one non-preferred carbon source, for example, a non-preferred sugar. As used herein, the term non-preferred carbon source refers to a carbon source that is metabolized by the native form of the organism at a rate of less than 0.01 g/hr/g cell mass, less than 0.005 g/hr/g cell mass, or less than 0.002 g/hr/g cell mass. Such a carbon source may be a carbohydrate, a sugar (e.g., glucose) or glycerol. Such a non-preferred carbon source may also be methanol. The non-preferred carbon source may also be an oxygen-containing organic compound. According to an embodiment, said non-preferred carbon source comprises at least 50%, at least 60%, at least 70%, at least 80% or at least 90% of said non-preferred carbon source. According to an embodiment, the concentration of said non-preferred carbon source in said provided fermentation medium is in a range between 2 g/L and 50 g/L.

According to an embodiment, said non-preferred sugar is selected from the group consisting of glucose, mannose, galactose, maltose, sucrose, lactose, cellobiose, and mixtures thereof. According to an embodiment, said non-preferred sugar comprises glucose.

According to an embodiment, glucose may be a non-preferred carbon source for wild-type *Clostridium ljungdahlii* or *C. autoethanogenum*. According to an embodiment, glucose may be metabolized at a rate greater than 0.01 g/hr/g cell mass for a clostridia species which has been genetically modified, e.g., to express a glucose-specific transmembrane transport enzyme, such as a phosphotransferase system (PTS) component.

According to an embodiment, said carbon source further comprises at least one preferred sugar. As used herein, the term preferred sugar refers to a sugar that is metabolized by the native form of the organism at a rate greater than 0.01 g/hr/g cell mass.

According to an embodiment, said preferred sugar is selected from the group consisting of fructose, xylose, arabinose, ribose, and mixtures thereof. According to an embodiment, said provided fermentation medium comprises said preferred sugar and said non-preferred sugar concurrently. According to an embodiment, said provided fermentation medium comprises first said preferred sugar and then said non-preferred sugar.

According to an embodiment, said non-preferred sugar is metabolized at a rate greater than 0.01 g/hr/g cell mass. Metabolism rates of a non-preferred sugar of greater than 0.01 g/hr/g cell mass may be achieved by an organism that has been genetically modified for increased non-preferred sugar metabolism. In an embodiment, said non-preferred sugar may be metabolized by a genetically modified organism at a rate greater than 0.02 g/hr/g (gram/hour/gram), greater than 0.04 g/hr/g cell mass, greater than 0.06 g/hr/g, greater than 0.08 g/hr/g cell mass, greater than 0.1 g/hr/g, greater than 0.12 g/hr/g cell mass, greater than 0.14 g/hr/g, greater than 0.16 g/hr/g cell mass, greater than 0.18 g/hr/g, greater than 0.2 g/hr/g cell mass, or greater than 0.26 g/hr/g.

According to an embodiment, metabolizing of the carbon source does not inhibit the metabolizing of the non-sugar reductant.

According to an embodiment, said provided fermentation medium comprises stillage of ethanol production. According to an embodiment, ethanol production includes fermentation of carbohydrates-containing feedstock to form a fermentation broth comprising ethanol, biomass and non-fermented components of the feedstock, e.g. carbon sources and proteins. According to an embodiment, ethanol is distilled out of said broth to form distilled ethanol and a residue comprising said biomass and non-fermented components of the feedstock. This residue is referred to as whole stillage. According to an embodiment, the provided fermentation medium comprises said whole stillage. Alternatively, the whole stillage is filtered or centrifuged to generate wet solids and a solids-depleted liquid referred to as thin stillage. According to an embodiment, the provided fermentation medium comprises said thin stillage. A typical thin stillage contains glycerol at about 36 gr/L, glucose, DP2, DP3 and DP4+ at 0.7 gr/L, 17 gr/L, 5 gr/L and 28 gr/L, respectively and lactic acid at 2.5 gr/L.

According to an embodiment, said carbon source and said non-sugar reductant are present in the fermentation medium at the same time. According to an embodiment, said fermentation medium comprises concurrently both said carbon source and said non-sugar reductant during at least a fraction of the culturing time, e.g., during at least 30% of the time, at least 40%, at least 50%, at least 60%, at least 70%, at least 80% or at least 90% of the time. The total reductant capacity of the non-sugar reductant is greater than 100% of the reductant efficiency the sugar alone could provide (e.g., >110%, >120%, >130%, >140%, >150%).

According to an embodiment, the method further comprises providing a fermentation medium comprising said carbon source and said non-sugar reductant. According to an embodiment, providing a fermentation medium comprises preparing an aqueous solution comprising said carbon source and said non-sugar reductant. According to an embodiment, providing comprises supplementing at least one of said carbon source and said non-sugar reductant during culturing. According to an embodiment, the fermentation medium comprises initially only the carbon source and then the non-sugar reductant is supplemented. According to an embodiment, supplementing said non-sugar reductant is done before the carbon source is fully utilized, e.g., at the time the carbon source is only 10%, 20%, 30% or 40% utilized.

According to an embodiment, said non-sugar reductant comprises a gaseous compound and said gaseous compound is supplemented to the fermentation medium, e.g., via bubbling the gaseous compound through the medium. The methods for supplementing the fermentation medium and/or the feedstock with a carbon source are not limited, and include, for example, exogenously feeding a gaseous compound, such as hydrogen, CO or $CO_2$ or adding a carbon source and/or feedstock and/or additional components to an initially provided fermentation medium or feedstock later in time during fermentation.

According to an embodiment, said fermentation medium is kept during at least a fraction of the culturing time at a super-atmospheric pressure, e.g., during at least 30% of the time, at least 40%, at least 50%, at least 60%, at least 70%, at least 80% or at least 90% of the time. According to an embodiment, said super-atmospheric pressure is in the range between about 1.1 bar and about 10 bar.

Co-Location Exemplary Embodiments

According to an embodiment said method is conducted at co-location with corn wet mill ethanol production or corn dry mill ethanol production. As used herein, the term co-location refers to location within 10 Km from each other, within 5 Km, within 2 Km or within 1 Km.

An exemplary co-location integrated method for producing ethanol is depicted in FIG. 1. It comprises, a primary ethanol fermentation [110] generating a primary ethanol stream [154] and stillage [156] and a secondary mixotrophic ethanol fermentation [120], wherein said stillage forms a fraction of the fermentation medium and wherein a secondary ethanol stream [184] is generated. According to an embodiment, the method further comprises milling [130] and liquefying [140] incoming corn grains [105] to form the feedstock [145] of the primary fermentation. According to an embodiment, the method further comprises fractionating the corn grains, e.g. for pre-removal of fiber and/or corn oil (not shown in the FIGURE). The liquefied-corn-containing primary fermentation medium is metabolized by an ethanol producing organism, e.g. a yeast, in [110]. A primary fermentation broth is formed [114] containing ethanol. In distillation columns [150], ethanol is distilled out, forming a primary ethanol stream [154], which is optionally further dried on molecular sieves (not shown in the FIGURE). The residue [156] is the whole stillage comprising the yeast, corn protein, optionally also fiber and oil, and soluble matter including glycerol and oligosaccharides. The whole stillage is centrifuged [160] to form wet distillers solids [166] and thin stillage [164].

The method further comprises gasification of corn stover [116] in a gasifier [170] to form a mixture of hydrogen, CO and $CO_2$ [175] to be used as non-sugar reductant. Said non-sugar reductant is combined with said thin stillage (the carbon source) to form the feedstock for the secondary fermentation [120] medium. This carbon source and the non-sugar reductant are metabolized by said naturally acetogenic organism capable of producing ethanol to form a secondary fermentation broth [121] comprising ethanol. According to an embodiment, ethanol is distilled out of the secondary fermentation broth in dedicated distillation columns [180]. Alternatively, at least a fraction of secondary broth distillation is combined with the primary broth distillation.

Fermentation Performance Exemplary Embodiments

According to an embodiment, the method is characterized in carbon yield of at least 70%, at least 80%, at least 90%, at least 100%, at least 110%, at least 120%, at least 130%, at least 140%, at least 150%, or at least 160%. As used herein carbon yield is calculated by total amount of carbon in produced bioproducts divided by the total amount of carbon metabolized from said carbon source. According to an embodiment, said bioproduct comprises ethanol and the method is characterized in carbon yield of at least 67%, at least 69%, at least 71%, at least 73% or at least 75%. According to an embodiment, said bioproduct is ethanol and the method is characterized in carbon yield of at least 67%, at least 69%, at least 71%, at least 73% or at least 75%, wherein carbon yield is calculated by total amount of carbon in produced ethanol divided by the total amount of carbon metabolized from said carbon source.

According to an embodiment, the method yields a greater amount of the at least one bioproduct than the at least one bioproduct produced by heterotrophic fermentation with the same organism under the same conditions.

According to an embodiment, the method yields a greater amount of the at least one bioproduct than the combined amounts of the at least one bioproduct produced by heterotrophic and autotrophic fermentation with the same organism under the same conditions. Said embodiment is exemplified by comparing three cases of fermenting with a given organism capable of and/or configured for use in the method. In the first case (referred to herein as heterotrophic fermentation), a microorganism is cultured in a fermentation medium comprising a carbon source to form a heterotrophic fermentation broth. In the second case (referred to herein as autotrophic fermentation), the microorganism is cultured in a fermentation medium comprising a non-sugar reductant to form an autotrophic fermentation broth. In the third case (referred to herein as supplemented mixotrophic fermentation), a microorganism is cultured in a fermentation medium comprising a mixture of the carbon source and the non-sugar reductant to form a mixotrophic fermentation broth. At the end of culturing time, the autotrophic fermentation broth is mixed with the heterotrophic fermentation broth to form a mixed fermentation broth. According to said embodiment, the supplemented mixotrophic fermentation method may achieve greater production of a target bioproduct or a combination of target bioproducts than the combined amounts produced by heterotrophic and autotrophic fermentation with the same microorganism under the same conditions. According to an embodiment, the supplemented mixotrophic fermentation method may achieve greater production of a target bioproduct or a combination of target bioproducts than a non-supplemented mixotrophic fermentation method with the same microorganism under the same conditions. The nature of bioproducts in said mixotrophic fermentation and/or the molar ratio between the bioproducts (in case of forming multiple bioproducts), may differ from those of the mixed fermentation broth.

According to an embodiment, the method produces at least one bioproduct and acetic acid as a second bioproduct and the amount of acetic acid produced per biomass unit weight is less than about 50% of that produced in autotrophic fermentation with the same organism under the same conditions.

According to an embodiment, the $^{13}C/^{12}C$ isotope ratio of the carbon present in the bioproduct is less than that of atmospheric $CO_2$. A $^{13}C/^{12}C$ isotope ratio may be used as an indicator of nutrient cycling. For example, according to an embodiment, said bioproduct is characterized by a $^{13}C/^{12}C$ isotope ratio of less than that of atmospheric $CO_2$. In such a case, the $^{13}C/^{12}C$ isotope ratio would be indicative of production of the bioproduct from a non-atmospheric $CO_2$ source, for example, CO, $CO_2$, carbonate, bicarbonate, methanol or mixtures thereof present in the non-sugar reductant.

According to an embodiment, said bioproduct is non-naturally occurring. As used herein a non-naturally occurring bioproduct is a product which is unattainable by said organism when cultured in autotrophic conditions or is produced from a metabolic pathway not native to said organism.

According to an embodiment, said bioproduct is selected from the group consisting of alcohols, organic acids and ketones. According to an embodiment, said bioproduct is selected from the group consisting of even numbered primary alcohols, odd numbered secondary alcohols, organic acids of less than 7 carbons, C3 compounds, C4 compounds, and mixtures thereof.

According to an embodiment, said bioproduct comprises ethanol. According to an embodiment, said bioproduct is ethanol.

According to an embodiment, said bioproduct comprises acetone. According to an embodiment, said bioproduct is acetone.

According to an embodiment, said bioproduct comprises isopropanol. According to an embodiment, said bioproduct is isopropanol.

According to an embodiment, said bioproduct comprises butanol. According to an embodiment, said bioproduct is butanol. According to an embodiment, said butanol is selected from the group consisting of normal butanol, isobutanol, secondary butanol and mixtures thereof.

According to an embodiment, said bioproduct comprises butyric acid. According to an embodiment, said bioproduct is butyric acid.

According to an embodiment, said bioproduct is selected from the group consisting of acetic acid, acetone, propionic acid, butyric acid, hexanoic acid, 3-hydroxypropionic acid, 3-hydroxybutyric acid, crotonic acid, acetoacetic acid, lactic acid, 2-hydroxyisobutyric acid, 3-methylbutanoic acid, ethanol, butanol, crotyl alcohol, hexanol, acetone, isopropanol, 2,3-butanediol, acetoin, 1,3-propanediol, and combinations thereof.

According to an embodiment, said broth comprises a first bioproduct and a second bioproduct, wherein said first bioproduct is selected from the group consisting of acetoacetic acid, acetone, isopropanol, 3-hydroxybutyric acid, 2-hydroxyisobutyric acid, and combinations thereof, said second bioproduct is selected from the group consisting of ethanol, butanol, crotyl alcohol, hexanol, and combinations thereof, and the molar ratio between said first bioproduct and said second bioproduct is in the range from 0.1 to 0.95.

Optionally said method further comprises separating said bioproduct from said broth. Any separation method is suitable. According to various embodiments, separating comprises distillation, solvent extraction, crystallization, ion-exchange, membrane separation and combinations thereof. In an embodiment, the bioproduct may be separated by evaporation, wherein evaporation means any transfer into the vapor phase, e.g., distillation, stripping, etc. In another embodiment, the bioproduct may be, for example, acetone, and the method includes catalytically converting said separated acetone into at least one acetone derivative. In an embodiment, such a method may comprise catalytically converting said separated acetone into one or more of mesitylene (1-3-5-trimethylbenzene), isophthalic acid, uvitic acid, and meta-xylene.

The subject matter disclosed herein provides advantages and combinations of features not previously achieved or even appreciated by prior fermentation or electricity-producing methods. For example, the subject matter disclosed herein integrates production of hydrogen via conventional electrolysis methods with mixotrophic fermentation processes that utilize such hydrogen in a feedstock for higher yields of bioproducts. Further to this, byproducts of the mixotrophic fermentation process may themselves be utilized as an energy source, i.e., a lignocellulosic biomass may, for example, be used to produce a carbohydrate solution and lignin—the carbohydrate solution may be utilized as part of a carbon source and the lignin produced during mixotrophic fermentation may be burned to generate power, which power can be transferred to a conventional power grid to provide energy/electricity for consumption by consumers or to generate more hydrogen.

Moreover, the hydrogen produced and the lignin that are produced may serve as energy stores for later use, such that the methods achieve additional utility. There is a huge difference between electricity demand during peak vs. off-peak hours. Utilizing methods as disclosed herein it is possible to burn lignin at desired times, e.g., during peak hours. Electricity from the grid may also be conveniently used during off-peak hours to produce hydrogen to be utilized immediately or stored for later use in mixotrophic methods as disclosed herein. Indeed, energy may be stored in the form of hydrogen or unused lignin. Lignin can be partially oxidized to generate hydrogen.

The methods disclosed herein are not limiting and are integrative. As disclosed above, methods as disclosed herein include features such as hydrogen production (e.g., from water at relatively high quality (with or without addition of acid) via conventional electrolysis methods), utilization of lignocellulosic material for bioproduct formation, and electricity or other energy production from the lignin produced via the disclosed fermentation methods.

It is particularly noteworthy here that the feedstocks are to be considered differently than those in previous mixotrophic applications, i.e., while the carbon source here does provide a source of carbon, the second "feedstock" is a reductant. And while sugars are reductants, the sugars disclosed herein are part of the carbon sources. The non-sugar reductants are electron donor other than sugars, e.g. hydrogen or carbon monoxide. It should also be noted that the carbon source can also comprise additional carbon sources such as glycerol, methanol and formates, and the $CO_2$ used as the carbon source can be in any form including carbonate, bicarbonate and urea.

Carbon yield as disclosed herein, is based on the total amount of carbon in produced bioproducts divided by the total amount of carbon metabolized from said carbon source. Such carbon yield is typically at least 50%, and for example, where the bioproduct comprises ethanol the carbon yield is typically at least 67%, for example greater than 69%, greater than 71%, greater than 73%, and greater than 75%.

In one embodiment disclosed herein, where the carbon source is a sugar, and the reductant comprises $H_2$, the weight/weight ratio between the sugar and the $H_2$ is typically in the range between about 2 and about 150, for example, 20 to 70, depending on how much ethanol comes from the gas with $H_2$ supplementation, for example. See below where representative ranges between 3.75 and 15 are demonstrated. The sugar and the $H_2$ may be provided currently at the start of fermentation such that the weight/weight ratio between the sugar and the $H_2$ is the starting point for fermentation. Alternatively, a particular weight/weight ratio between the sugar and the $H_2$ may be maintained throughout fermentation or achieved part way into fermentation.

EXAMPLE 1

Calculation of $Wt_{sugar}/Wt_{H2}$ $$\frac{Wt-Sugar}{Wt-H2} = \frac{MW-sugar * \text{moles of sugar consumed}}{MW-H2 * \left(\frac{6 \text{ mole } H2}{1 \text{ mol } EtOH} * \text{moles } EtOH \text{ from gas}\right)}$$

For example, in a mixotrophic fermentation process with $H_2$ supplementation, the moles of ethanol (EtOH) which can be produced from gas is 1 mole (the two moles of $CO_2$ which can be produced from glycolysis can be fixed into one additional mole of EtOH). So the calculation is:

$$\frac{Wt-Sugar}{Wt-H2} = \frac{180 \text{ g/mol} * 1 \text{ mole sugar}}{2 \text{ g/mol} * \left(\frac{6 \text{ mole } H2}{1 \text{ mol } EtOH} * 1 \text{ mole } EtOH \text{ from gas}\right)} = 15$$

EXAMPLE 2

Calculation of $Wt_{sugar}/Wt_{H2}$

Another example, in a mixotrophic fermentation process with sugar supplementation, the total number of moles of ethanol (EtOH) from gas is 4 moles (six moles of exogenous $CO_2$ is fixed into three moles of EtOH and the two moles of $CO_2$ which can be produced from glycolysis can be fixed into one additional mole of EtOH). So the calculation is:

$$\frac{Wt-Sugar}{Wt-H2} = \frac{180 \text{ g/mol} * 1 \text{ mole sugar}}{2 \text{ g/mol} * \left(\frac{6 \text{ mole } H2}{1 \text{ mol } EtOH} * 4 \text{ mole } EtOH \text{ from gas}\right)} = 3.75$$

EXAMPLE 3

Total Reductant Efficiency ($RE_{total}$)

To define RE, CR [=] available reductant (electrons) per carbon $$CR = \frac{[(\#C*4) + \# H - (2*\#O)]}{\#C}$$

So for sugar, $CR_{sugar} = 4$ $$CR-sugar = \frac{[(6*4) + 12 - (2*6)]}{6} = 4$$

$$RE-total = \frac{(\text{mole of ethanol produced}) * (2 \text{ C per mole ethanol}) * CR - \text{ethanol}}{(\text{mole of sugar}) * (6 \text{ C per mole sugar}) * (CR - \text{sugar}) + \#H \text{ gas consumed}}$$

For the case where $H_2$ is added but no mixotrophy takes place:

$$RE-total = \frac{(2) * (2 \text{ C per mole ethanol}) * 6}{(1) * (6 \text{ C per mole sugar}) * (4) + 12} = 0.6667$$

Thus the minimum $RE_{total}$ is >66.7%. If only one $CO_2$ is fixed into ethanol, the efficiency is 83%. If both $CO_2$ are fixed, the efficiency is 100%.

EXAMPLE 4

Sugar Reductant Efficiency ($RE_{sugar}$)

To determine sugar reductant efficiency:

$$RE-sugar = \frac{(\text{mole of ethanol produced}) * (2 \text{ C per mole ethanol}) * CR - \text{ethanol}}{(\text{mole of sugar}) * (6 \text{ C per mole sugar}) * (CR - \text{sugar})}$$

For conventional ethanol fermentation.

$$RE-sugar = \frac{(2) * (2 \text{ C per mole ethanol}) * 6}{(1) * (6 \text{ C per mole sugar}) * (4)} = 1.0$$

For the mixotrophic method disclosed herein with $H_2$ supplementation $$RE-sugar = \frac{(3) * (2 \text{ C per mole ethanol}) * 6}{(1) * (6 \text{ C per mole sugar}) * (4)} = 1.5$$

Thus the minimum $RE_{sugar}$ is >100% for mixotrophy to occur.

EXAMPLE 5

*Clostridium ljungdahlii* Mixotrophic Fermentation with $H_2$ Supplementation

*Clostridium ljungdahlii* (DSM 13528) is grown in 20 ml of standard PETC medium (5 g/l of glucose) at 37° C. at 150 rpm. The headspace (~140 ml) is charged to 30 psig with a gas mixture of 27% $H_2$, 4% $CO_2$, and the balance is $N_2$. The bottles are inoculated (10% v/v inoculum) with an exponentially growing culture ($OD_{600}$~0.8-1.0) and sampled as indicated (Table 1). Supernatant samples are analyzed by HPLC.

TABLE 1

Metabolite production in *C. ljungadhlii* (average, n = 4)

| | | Concentration (g/L)(grams per liter) | | | | |
|---|---|---|---|---|---|---|
| Hour | $OD_{600}$ | Glucose | Lactate | Acetate | 2,3-Butanediol | Ethanol |
| 0 | 0.185 | 4.91 | 0.01 | 0.20 | 0.00 | 0.04 |
| 24 | 0.659 | 4.00 | 0.02 | 1.11 | 0.00 | 0.28 |
| 43 | 1.17 | 2.91 | 0.02 | 1.47 | 0.00 | 1.33 |
| 116 | 1.00 | 0.36 | 0.02 | 1.53 | 0.03 | 3.31 |
| 163 | 0.50 | 0.35 | 0.02 | 1.52 | 0.03 | 3.35 |

In addition to metabolite analysis, the headspace gas is also sampled and a total of 3.41 mmol of $H_2$ is consumed.

The total amount of glucose consumed is 25.3 mM, and the total amount of ethanol produced is 71.9 mM. For every mole of glucose consumed two moles of ethanol can be produced to give a maximum amount of ethanol from glucose as 50.6 mM. Therefore, the minimal amount of ethanol from gas is 21.3 mM. Calculating the $Wt_{sugar}/Wt_{H2}$ gives:

$$\frac{Wt - \text{Sugar}}{Wt - \text{H2}} = \frac{180 \frac{\text{g}}{\text{mol}} * 0.0253 \text{ M sugar}}{2 \text{ g/mol} * \left(\frac{6 \text{ mole H2}}{1 \text{ mol } EtOH} * 0.0213 \text{ } MEtOH \text{ from gas}\right)} = 17.82$$

To calculate the $RE_{total}$:

$$RE - \text{total} = \frac{(0.0719 \text{ M}) * (0.02 \text{ L}) * (2 \text{ C per mole ethanol}) * 6}{(0.0253 \text{ M}) * (0.02 \text{ L}) * (6 \text{ C per mole sugar}) * (4) + 0.00682 \text{ mol H}} = 0.91$$

To calculate the $RE_{sugar}$:

$$RE - \text{sugar} = \frac{(0.0719 \text{ M}) * (0.02 \text{ L}) * (2 \text{ C per mole ethanol}) * 6}{(0.0253 \text{ M}) * (0.02 \text{ L}) * (6 \text{ C per mole sugar}) * (4)} = 1.42$$

The total carbon yield is 1.04, and the ethanol carbon yield is 0.79.

EXAMPLE 6

*Clostridium autoethanogenum* Mixotrophic Fermentation with $H_2$ Supplementation

*Clostridium autoethanogenum* (DSM 10061) is grown in 20 ml of standard PETC medium (5 g/l of glucose) at 37° C. at 150 rpm. The headspace (~140 ml) is charged to 30 psig with a gas mixture of 27% $H_2$, 4% $CO_2$, and the balance is $N_2$. The bottles are inoculated (10% v/v inoculum) with an exponentially growing culture ($OD_{600}$ 0.8-1.0) and sampled as indicated (Table 2). Supernatant samples are analyzed by HPLC.

TABLE 2

Metabolite production in *C. autoethanogenum* (average, n = 4)

| | | Concentration (g/L)(grams per liter) | | | | |
|---|---|---|---|---|---|---|
| Hour | $OD_{600}$ | Glucose | Lactate | Acetate | 2,3-Butanediol | Ethanol |
| 0 | 0.174 | 5.24 | 0.01 | 0.14 | .000 | 0.06 |
| 24 | 0.343 | 4.69 | 0.04 | 0.43 | 0.03 | 0.19 |
| 43 | 0.870 | 3.72 | 0.05 | 0.61 | 0.09 | 1.01 |
| 116 | 1.26 | 0.01 | 0.03 | 0.54 | 0.32 | 3.93 |
| 163 | 1.09 | 0.01 | 0.03 | 0.54 | 0.33 | 4.06 |

In addition to metabolite analysis, the headspace gas is also sampled, and a total of 3.43 mmol (millimole) of $H_2$ is consumed.

The total amount of glucose consumed is 29.0 mM, and the total amount of ethanol produced is 86.9 mM. For every mole of glucose consumed two moles of ethanol can be produced to give a maximum amount of ethanol from glucose as 58.1 mM (millimole). Therefore, the minimal amount of ethanol from gas is 28.8 mM. Calculating the $Wt_{sugar}/Wt_{H2}$ gives:

$$\frac{Wt - \text{Sugar}}{Wt - \text{H2}} = \frac{180 \frac{\text{g}}{\text{mol}} * 0.0290 \text{ M sugar}}{2 \text{ g/mol} * \left(\frac{6 \text{ mole H2}}{1 \text{ mol } EtOH} * 0.0288 \text{ } MEtOH \text{ from gas}\right)} = 15.11$$

To calculate the $RE_{total}$:

$$RE - \text{total} = \frac{(0.0869 \text{ M}) * (0.02 \text{ L}) * (2 \text{ C per mole ethanol}) * 6}{(0.0290 \text{ M}) * (0.02 \text{ L}) * (6 \text{ C per mole sugar}) * (4) + 0.00685 \text{ mol H}} = 1.00$$

To calculate the $RE_{sugar}$:

$$RE - \text{sugar} = \frac{(0.0869 \text{ M}) * (0.02 \text{ L}) * (2 \text{ C per mole ethanol}) * 6}{(0.0290 \text{ M}) * (0.02 \text{ L}) * (6 \text{ C per mole sugar}) * (4)} = 1.50$$

The total carbon yield is 0.99, and the ethanol carbon yield is 0.85.

Mixotrophy generally combines the attributes of heterotrophy and autotrophy. As disclosed in the above examples, the carbon source is sugar and $CO_2$ that is generated in the metabolysis. As disclosed herein, the $CO_2$ is reduced because of its high oxidation capacity. Sugar can also act as a reductant to a certain extent, but can't reduce all the $CO_2$ produced. This is what generally occurs in non-supplemented mixotrophy, using what the sugar can provide for reducing the $CO_2$. That will provide up to a certain carbon yield. But that process doesn't generally improve yield with ethanol, for example, in the case of non-supplemented mixotrophy. But adding a reducing agent such as hydrogen adds reducing capacity beyond what sugar can provide. In certain instances, this can improve yield from 50% to 75% for example. As a result, more bioproduct can be obtained from the sugars which can represent the most expensive consumable in the production process.

If the supplemented mixotrophic process as disclosed herein is set up next to a conventional ethanol production facility, for example, the supplemented process can use the excess $CO_2$ generated in the conventional process. Typically, 100 weight units of sugar converts into about 50 weight units of ethanol and about 50 weight units of $CO_2$. So not only can the supplemented process produce a greater percentage of ethanol, but can use the $CO_2$ generated in a conventional process to generate more ethanol. Use of hydrogen improves the yield.

At its first level, the use of reductant as disclosed herein improves significantly the yield over conventional ethanol production and non-supplemented mixotrophy. At a second level, the supplemented process can use $CO_2$ from exogenous sources. Not being satisfied with just the reducing capacity of the sugar, addition of reductant is key. Sugar is the carbon source, its main function, and while it has some reducing capacity, it is not enough for what is accomplished with the supplemented mixotrophic processes disclosed herein, utilizing a reductant agent that is not the sugar. The simple addition of more sugar for its reducing function produces more $CO_2$, so its help as a reducing agent even though it has reducing properties is limited. Some $CO_2$ is generated in the metabolism of sugar, and some $CO_2$ can be added to consume reductant, but it is noteworthy that the supplemented process disclosed herein lowers the carbon footprint not only for the supplemented mixotrophic process, but can also do so in conjunction with conventional ethanol production processes as well, in addition to improving the efficiency/yield of existing processes (works with sugar which is favored, but other carbon sources such as glycerol as well). The amount of $CO_2$ which can be added depends on the amount of sugar present, and more reductant can be added to accommodate added $CO_2$ as well.

Ideally 100% of the reducing capacity of the reductant is utilized. But the supplemented mixotrophic process clearly attains greater than 100% of the reducing capacity of what the sugar alone is capable of attaining. And carbon yield is also more that 100% of what the sugar can provide, because of added $CO_2$, for example. So clearly higher/added carbon yield and higher/added reducing capacity over what the sugar alone can provide, based on $CO_2$ addition and hydrogen addition, is attained.

Glucose has one oxygen per carbon atom, ethanol has two carbons per oxygen atom, so with conventional processes excess oxygen is released in the conversion in the form of $CO_2$. With the supplemented mixotrophic process, this emitted $CO_2$ is captured and is used as another carbon source for the supplemented mixotrophic process. While this has been generally disclosed for ethanol, the same would apply to other bioproducts in addition to ethanol, where $CO_2$ is produced and where added hydrogen, for example, can improve yield.

Thus, the scope of the invention shall include all modifications and variations that may fall within the scope of the attached claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A supplemented mixotrophic fermentation method comprising
    i. providing a naturally acetogenic organism capable of metabolizing a sugar and $H_2$ for producing ethanol;
    ii. providing a fermentation medium comprising a carbon source and a non-sugar reductant wherein said carbon source consists of a sugar that is metabolized by the native form of the organism at a maximum rate of less than 0.01 g/hr/g cell mass; and wherein said non-sugar reductant consists of $H_2$ at weight/weight ratio between said sugar and said $H_2$ in the range between 1.20 and 150; and
    iii. culturing said organism in said fermentation medium, whereby both the carbon source and the non-sugar reductant are metabolized and a fermentation broth comprising ethanol is formed, and wherein:
        a. the carbon yield based on the total amount of carbon in produced ethanol divided by the total amount of carbon metabolized from said carbon source is at least 67%;
        b. the total reductant efficiency is at least 67%; or
        c. $CO_2$ is emitted from a fermenter during culturing, and a weight/weight ratio between ethanol in said fermentation broth and the amount of emitted $CO_2$ is greater than 1.05.

2. The method of claim 1, comprising adding to said fermentation medium a mixture of $CO_2$ and hydrogen at a molar ratio in the range of from 1:0.1 to 1:15.

3. The method of claim 1, wherein said sugar comprises glucose or sucrose, wherein metabolizing the sugar produces $CO_2$, and wherein the organism metabolizes the $CO_2$ produced.

4. The method of claim 1, wherein said sugar consists of a mixture of glucose and sucrose, and wherein the organism metabolizes the $CO_2$ produced.

5. The method of claim 1, wherein said fermentation medium comprises stillage of ethanol production.

6. The method of claim 1, further comprising gasification of a corn processing co-product, whereby said non-sugar reductant is generated.

7. The method of claim 1, co-located with ethanol production.

* * * * *